US012697023B2

(12) United States Patent
Trumm et al.

(10) Patent No.: US 12,697,023 B2
(45) Date of Patent: Aug. 4, 2026

(54) METHOD, DEVICE, AND COMPUTER PROGRAM PRODUCT FOR DETERMINING A SENSITIVITY OF AT LEAST ONE EYE OF A TEST SUBJECT

(71) Applicant: Rodenstock GmbH, Munich (DE)

(72) Inventors: Stephan Trumm, Munich (DE); Adam Muschielok, Munich (DE); Wolfgang Becken, Neuried (DE); Yohann Bénard, Munich (DE); Anne Seidemann, Munich (DE)

(73) Assignee: Rodenstock GmbH, Munich (DE)

( * ) Notice: Subject to any disclaimer, the term of this patent is extended or adjusted under 35 U.S.C. 154(b) by 477 days.

(21) Appl. No.: 18/549,306

(22) PCT Filed: Mar. 11, 2022

(86) PCT No.: PCT/EP2022/056357
§ 371 (c)(1),
(2) Date: Sep. 6, 2023

(87) PCT Pub. No.: WO2022/189642
PCT Pub. Date: Sep. 15, 2022

(65) Prior Publication Data
US 2024/0148245 A1 May 9, 2024

(30) Foreign Application Priority Data

Mar. 12, 2021 (DE) .......................... 102021202442.4

(51) Int. Cl.
*A61B 3/036* (2006.01)
*A61B 3/00* (2006.01)
(52) U.S. Cl.
CPC ............ *A61B 3/036* (2013.01); *A61B 3/0025* (2013.01)

(58) Field of Classification Search
CPC .... G02C 7/022; G02C 7/083; G02C 2202/22; G02C 7/02; G02C 7/027; A61B 3/1015;
(Continued)

(56) References Cited

U.S. PATENT DOCUMENTS

2012/0092614 A1    4/2012  Drobe et al.
2016/0327808 A1   11/2016  Hatanaka
(Continued)

FOREIGN PATENT DOCUMENTS

CN        102713728 A    10/2012
CN        111133369 A     5/2020
(Continued)

OTHER PUBLICATIONS

Jun. 22, 2022 (PCT) PCT International Search Report and Written Opinion—App. PCT/EP2022/056357.
(Continued)

*Primary Examiner* — Brandi N Thomas
(74) *Attorney, Agent, or Firm* — Banner & Witcoff, Ltd.

(57) ABSTRACT

A method for determining a sensitivity of at least one eye of a test subject, including: determining a subjective refraction result for the at least one eye of the test subject; while determining the subjective refraction result, determining a first visual acuity of the at least one eye for a first applied refraction; while determining the subjective refraction result, determining a second visual acuity of the at least one eye for a second applied refraction, wherein the second applied refraction is different from the first applied refraction; and ascertaining the sensitivity of the at least one eye, considering the first and second visual acuities at the first and second applied refractions.

16 Claims, 3 Drawing Sheets

(58) Field of Classification Search
CPC . A61B 3/0033; A61B 3/0285; G02F 2203/28;
G02F 1/29; G02F 1/13452; G02F 1/1345;
G02F 1/134309
See application file for complete search history.

(56) References Cited

U.S. PATENT DOCUMENTS

| | | |
|---|---|---|
| 2017/0265738 A1 | 9/2017 | Keita et al. |
| 2020/0241320 A1 | 7/2020 | Bercher et al. |
| 2024/0423467 A1* | 12/2024 | Trumm .................. A61B 3/032 |

FOREIGN PATENT DOCUMENTS

| | | |
|---|---|---|
| CN | 111919159 A | 11/2020 |
| CN | 112449687 A | 3/2021 |
| EP | 2499534 B1 | 10/2016 |

OTHER PUBLICATIONS

Apr. 10, 2026 (CN) Office Action and Search Report—App. 202280020557.4.

* cited by examiner

METHOD, DEVICE, AND COMPUTER PROGRAM PRODUCT FOR DETERMINING A SENSITIVITY OF AT LEAST ONE EYE OF A TEST SUBJECT

TECHNICAL FIELD

The invention relates to a method, a device and a computer program product for determining a sensitivity of at least one eye of a test subject.

BACKGROUND

The sensitivity of an eye is understood as the dependence of the visual acuity of this eye on a misrefraction. The misrefraction is a deviation from the ideal refraction for the eyes. In other words, sensitivity describes how much the visual acuity changes when an optical correction placed in front of the eye changes.

The sensitivity of one or both eyes of a test subject can be taken into account when calculating and/or creating custom eyeglass lenses, in particular when creating multifocal eyeglass lenses such as ophthalmic eyeglass lenses. Eyeglass lenses can have transitions between areas with different optical corrections, e.g., transitions between a viewpoint for distance and a viewpoint for near vision. It is precisely these transitions between eyeglass lens areas with different optical corrections that can be designed differently. Here, reference is made, for example, to hard transitions or soft transitions, depending on how strong or gentle the change in refraction is along the transition. In the case of highly custom and high-quality eyeglass lenses, such a transition in particular (but other areas of the lens) can be adjusted to the sensitivity of the eye(s) of the eyeglass wearer.

To create highly custom and high-quality eyeglass lenses, knowledge of the sensitivity is therefore helpful. Conventionally, sensitivity is measured by first determining the visual acuity at the determined subjective refraction after determining the subjective refraction. Subsequently, the visual acuity is determined once again at a refraction that deviates from the determined subjective refraction by a specified distance of exactly 0.5 diopters. Thus, the measurement of a second visual acuity value is dependent on the determined subjective refraction value. The sensitivity can be determined from the two visual acuity values determined in this way for the two different refraction values.

SUMMARY

An object of the invention is to improve and/or simplify the determination of a sensitivity.

This object is achieved by the subject matters of the independent claims. Preferred embodiments are the subject matters of the dependent claims.

One aspect relates to a method for determining a sensitivity of at least one eye of a test subject. Here, a determination of a subjective refraction result for the at least one eye of the test subject is performed. While performing the determination of the subjective refraction result, a first visual acuity of the at least one eye for a first applied refraction is determined. Furthermore, while performing the determination of the subjective refraction result, a second visual acuity of the at least one eye for a second applied refraction is determined. The second applied refraction is different from the first applied refraction. Finally, the sensitivity of the at least one eye is ascertained taking into account the first and second visual acuities at the first and second applied refractions.

In the method, the individual method steps do not necessarily have to be carried out in the order listed above. This means that the individual method steps can take place either in the listed order, in a different order and/or also at least partially simultaneously.

In the method, the at least two required visual acuity values for the two different applied refractions are already determined during the performance of the determination of the subjective refraction result. The determination of the subjective refraction result can essentially be performed in a conventional and/or known manner. In such a determination of the subjective refraction result, the refractive power of the optical correction is determined with which the eye(s) of a test subject produce a sharp image of a visual object located, for example, in the distance. This determination can also be shortened to "performing a subjective refraction". There are standardized methods for performing the subjective refraction. These methods are performed by a refractionist, such as an optician or an ophthalmologist. For this purpose, measuring devices such as trial glasses, test lenses and/or a phoropter are conventionally used. The measuring devices can be operated either manually or electrically by the refractionist.

When determining the subjective refraction result, the subjective visual impression of the test subject is decisive for determining the required optical correction. In this process, the test subject communicates with the refractionist by giving them feedback regarding a visual task they have been given. The determination of the subjective refraction result can also be performed partially or completely automatically in the method according to the invention.

Conventionally, when determining sensitivity, the subjective refraction result is determined first and the visual acuity is determined with this subjective refraction, i.e., with an optical correction with refraction values that correspond to the subjective refraction result. Subsequently, the optical correction pre-designed for the eye(s) is changed by a predetermined distance and the visual acuity is determined a second time with this changed refraction, which is thus worse for the test subject. This means that in the conventional method, the determination of the sensitivity can only occur after the subjective refraction result has been ascertained.

In the method according to the invention, however, at least two different visual acuity values are already determined during the ascertaining of the subjective refraction result. This allows the sensitivity to be ascertained already during the subjective refraction and speeds up the determination procedure. With the method, at least the additional step of measuring the visual acuity at a given refraction distance can be dispensed with; the additional visual acuity is not determined only after finding the subjectively best refraction at one or more defined foggings, but is already acquired at least once during the refraction process.

The first and/or second visual acuity can be determined, for example, by displaying optotypes to the test subject. The visual acuity depends on which optotypes the test subject can recognize at the set, applied refraction.

After the determination of the subjective refraction result has been completed, the sensitivity can be determined on the basis of the measured first and second visual acuity values and the first and second refraction values. In particular, the distance of the first applied refraction from the determined subjective refraction result can be taken into account and/or the distance of the second applied refraction from the determined subjective refraction result. Since the subjective refraction result is not yet known when determining the first visual acuity and/or the second visual acuity, the distance of the first applied refraction or the second applied refraction from the subjective refraction result is also not yet known when determining the first and/or second visual acuity.

While the conventional method of determining sensitivity uses a fixed distance from the subjective refraction result to determine a visual acuity value at that fixed distance, the method is free from the use of a fixed distance from the subjective refraction result. Thus, the sensitivity is calculated on the basis of two visual acuity values, which may have been determined for two different refractions selected largely at random.

However, the first and second applied refractions fulfil at least the minimum condition that they deviate from each other in the sphere and/or in the cylinder. The deviation is at least a quarter of a diopter and/or a rotation of the cylinder axis by at least 45°. A quarter of a diopter is usually the smallest possible step from one optical correction to the next when determining subjective refraction. In the same way, the cylinder axes are usually rotated in 45° steps. The use of this minimum distance is necessary to ensure that the first refraction is actually different from the second refraction. In principle, this minimum distance can already be sufficient to determine the sensitivity. Preferably, the first refraction is more different from the second refraction, as detailed below.

When determining the subjective refraction result, different optical corrections, i.e., refractions, are used, which are displayed to the test subject. In principle, the applied refractions can have any optical effects that do not yet have to be adjusted to the test subject's eye(s). The visual acuity determination can be easily integrated into the process of determining the subjective refraction. For example, the subjective refraction result can be determined directly with the help of optotypes. Depending on the size and/or the distance of the optotypes from the test subject and/or the optical correction currently used, the visual acuity can thus be easily determined in the course of determining the subjective refraction. Two visual acuity values, for example the first visual acuity and the second visual acuity, may already be sufficient to determine the sensitivity. However, more than these two visual acuity values can be determined in the course of determining the subjective refraction. This allows the sensitivity determined in this way to be determined more accurately.

When calculating the sensitivity from the data obtained during the determination of the subjective refraction, a first distance of the first applied refraction from the determined subjective refraction can first be determined and/or a second distance of the second refraction from the determined subjective refraction. This distance can be zero for at least one of the two visual acuity values, i.e., the first refraction or the second refraction can also correspond to the determined subjective refraction. The method thus also includes at least the possibility of determining the visual acuity at the specific subjective refraction and of using and/or taking into account this visual acuity value at the subjective refraction when calculating the sensitivity.

The method can accelerate and/or simplify the determination of sensitivity. This applies to both the refractionist and the test subject, who no longer has to make an additional visual acuity test after determining the most favorable optical correction for them in order to determine the visual acuity with a predetermined misrefraction.

Within the scope of this application, the terms visual acuity and visual acuity value may be used interchangeably, as may the terms refraction and/or refraction value and/or optical correction. The term subject refraction result can be used interchangeably with the term subjective refraction. The terms first and second applied refraction can be used interchangeably with the terms first and second refraction, optical correction and/or applied optical effect.

According to one embodiment, the first visual acuity is determined before the subjective refraction result for the at least one eye is determined. In this embodiment, the first refraction differs from the subjective refraction determined during the method. The first applied refraction, for which the first visual acuity is determined, can in principle be any distance from the determined subjective refraction. Since the method does not require a fixed distance of the first refraction from the subjective refraction, the distance of the first refraction from the subjective refraction is essentially not predefined, nor is the distance between the first and second refraction and the distance of the second refraction from the subjective refraction. Therefore, a refraction with a random distance from the subjective refraction can be chosen as the first refraction and/or second refraction.

According to a further development of the embodiment, the determined subjective refraction result is used as the second applied refraction and the second visual acuity is determined for the determined subjective refraction result. The determination of the subjective refraction can overlap and/or be carried out simultaneously with the determination of the second visual acuity value. Thus, to determine the sensitivity, the visual acuity at the specific subjective refraction is provided, which is used as the second refraction, and furthermore the first visual acuity at the deviating first refraction. Thus, in principle, sufficient data is provided to calculate the sensitivity of at least one eye of the test subject.

According to one embodiment, the sensitivity of the at least one eye is ascertained on the basis of a sensitivity metric, and this ascertainment of the sensitivity is carried out from visual acuity measurements at applied refraction values that do not have a distance from one another and/or from the refraction result that is specifically predetermined and/or optimized for ascertaining the sensitivity. In this case, the determination of the sensitivity is independent of a visual acuity measurement at a given distance of applied refraction values from each other and/or from the refraction result. Instead, the refraction values and associated visual acuity measurements obtained during the refraction process and, if necessary, the refraction result are used to determine sensitivity. In conventional refraction methods, these refraction and visual acuity values are not even determined, with the exception of the refraction result, as only the latter is of interest here. In conventional methods of refraction determination, sensitivity is determined by performing at least one additional visual acuity measurement at an applied refraction different from the subjective refraction result after determining the refraction result. This differing applied refraction has a predetermined distance from the subjective refraction result. However, the embodiment makes it possible not to have to perform an additional measurement initially, since by using a sensitivity metric, a sensitivity can be calculated even if the applied refraction values and/or the subjective refraction result do not have a predetermined distance from each other.

The sensitivity metric is a distance function that assigns a value to two refraction values, which is defined as the distance between these two refraction values. The sensitivity metric may be defined in the metric space of refraction values. Each refraction value of the sensitivity metric may have a visual acuity value associated therewith. The refraction can, for example, be defined in at least three-dimensional space. Thus, a refraction value can usually be described with the coordinates s, c and α. Here, s can be dependent on the strength of an optical correction of the sphere, c can be dependent on the strength of an optical correction for a cylinder, and a can be dependent on the axial position of this cylinder. In this metric space of refraction values, at least the visual acuity values for the first refraction and the second refraction are determined and are therefore known when calculating the sensitivity. The sensitivity metric can be used to determine the sensitivity as a function of two fundamentally arbitrary different refraction values. By using such a sensitivity metric, the determination of sensitivity becomes independent of visual acuity measurements at given refraction values, as is common with conventional methods. In this case, the determination of the sensitivity can, on the one hand, become independent of visual acuity measurements at at least one predetermined and/or fixed refraction distance from the refraction result and, on the other hand, of visual acuity measurements at at least one predetermined and/or fixed relative refraction distance between the two applied refractions. This can make it easier for both the refractionist and the test subject to obtain the measurement data needed to determine sensitivity.

If the sensitivity determined in this way has not yet been determined with sufficient accuracy, which can be determined on the basis of a predefined threshold value for the accuracy of the sensitivity determination, according to a further embodiment, in addition to the refraction values already provided and accumulated during the refraction process and/or the refraction result together with the associated visual acuity measurements, one or more additional visual acuity measurement(s) can be performed for refraction values that have a predefined distance from the refraction result that is particularly favorable for the sensitivity determination. Such a particularly favorable distance of the refraction value can be based on the measurement accuracy of the refraction and, for example, be a multiple thereof (e.g., 1, 1.5, 2, 3 or 4 times the measurement accuracy measured as dioptric distance). The refraction values are preferably selected in such a way that accommodation of the measured person during the measurement leads to a deterioration of visual acuity, in particular such that the additional visual acuity measurement(s) take(s) place with more positive refraction values than the refraction result. More positive refraction values can be understood as refraction values whose spherical equivalent, or more advantageously whose both main sections (sphere+cylinder and sphere−cylinder) are larger than the corresponding quantities formed from the refraction result.

According to one embodiment, different optotypes are displayed for determining the subjective refraction result, and while determining the subjective refraction result, a visual acuity belonging to the displayed optotypes is determined as the first and/or second visual acuity. In this way and manner, the visual acuity determination can be easily and smoothly integrated into the determination of subjective refraction. In this case, the determination of a visual acuity value for a refraction that deviates from the subjective refraction can be carried out almost automatically as part of the determination of the subjective refraction. The visual acuity value determined in this way can be easily written down and/or stored for later use in ascertaining the sensitivity. The use of the optotypes also allows more than just the first or second visual acuity value to be ascertained and/or written down and/or stored when determining subjective refraction. By taking more than two visual acuity values into account, the determination of sensitivity can be further improved. The visual acuity value associated with the optotypes can be determined taking into account the distance of the displayed optotypes from the test subject's eye and/or the optical correction as well as the size of the displayed optotypes. The determination of the visual acuity values is essentially known and will therefore not be described in detail here.

According to one embodiment, the first applied refraction has a distance from the second applied refraction of at least half a diopter in the sphere and/or of at least one diopter of a cylinder. Such a minimum distance leads to particularly good results when ascertaining the sensitivity. Therefore, it is preferable to use the visual acuity values for two refractions that have such a minimum distance in the sphere and/or in the cylinder.

In one embodiment, after determining the subjective refraction result, it is checked whether the first applied refraction has a predetermined spherical and/or cylindrical minimum distance from the second applied refraction. In the event that this predetermined minimum distance is not reached, a third visual acuity for a third applied refraction is determined which is spaced apart from the first and/or second applied refraction at least by the predetermined minimum distance. The sensitivity of the at least one eye is ascertained taking into account the third visual acuity at the third applied refraction. The sensitivity can also be determined by taking all three visual acuity values into account. Even though in this exemplary embodiment an additional visual acuity measurement is performed downstream of the determination of the subjective refraction, this embodiment nevertheless offers the possibility of simplifying and/or shortening the determination of the sensitivity. This applies in particular to the case where the first refraction maintains the predetermined spherical and/or cylindrical minimum distance from the second refraction. The predetermined minimum distance can be, for example, half a diopter in the sphere and/or a whole diopter in the cylinder. In the case where the minimum distance between the first and second refraction is provided, the determination of the third refraction can be dispensed with. Therefore, this method still offers the option of a shortened and/or simplified sensitivity determination. This shortening and/or simplification is made possible by checking the minimum distance downstream of the subjective refraction determination.

According to one embodiment, the sensitivity of the at least one eye is ascertained on the basis of a linear model in which a dependence of the sensitivity for a cylindrical refraction distance on the sensitivity for a spherical refraction distance is assumed. If this assumption is made, i.e., that the sensitivity for a cylindrical refraction distance depends on the sensitivity for a spherical refraction distance, the sensitivity can already be determined on the basis of the two visual acuity values for the two different refractions. This linear model represents a simplified model. A correlation between the spherical and cylindrical refraction distance is assumed, which is reflected in the dependence of the sensitivities. Therefore, this linear model of a sensitivity metric is particularly advantageous when only the two visual acuity values are ascertained. This greatly simplifies the determination of sensitivity.

According to one embodiment, a third visual acuity of the at least one eye for a third applied refraction is determined. The sensitivity of the at least one eye is ascertained taking into account the first, second and third visual acuities at the first, second and third applied refractions on the basis of a bilinear model. The bilinear model of the sensitivity metric is somewhat more complex than the previously mentioned linear model. It requires at least three visual acuity values at three different refractions for the calculation of the sensitivity. In this embodiment, the first refraction differs from the first refraction, from the second refraction and also from the third refraction. The second refraction also differs from the third refraction. Put simply, all three refraction values differ from each other. This provides three measured values of visual acuity in the sensitivity metric on the basis of which the sensitivity can be ascertained. This improves the accuracy of the determination of the sensitivity compared to the previously mentioned linear model. The bilinear model is also based on an approximation, but already provides significantly better results than the linear model. The third visual acuity can also be determined during the determination of the subjective refraction. Alternatively, the third visual acuity can be ascertained only after the subjective refraction has been determined, e.g., at a predetermined distance from the first and/or second refraction and/or the subjective refraction.

Both the linear model and the bilinear model of the sensitivity metric can take empirical measurement data into account, i.e., in particular dependencies of the sensitivity on the sphere, on the cylinder and/or on the axis position. This empirical data can furthermore be dependent on the age of the test subjects in order to adjust the linear and/or bilinear model to the age of the test subject. In doing so, the determination of sensitivity can be improved if necessary.

According to one embodiment, the sensitivity is ascertained without consideration of the specific subjective refraction result. Thus, the sensitivity is not determined taking into account a distance of the first and/or second refraction from the subjective refraction, but on the basis of the distance of at least two visual acuity values from each other, e.g., on the basis of the distance of the first visual acuity from the second visual acuity. The distance of the two visual acuity values from the subjective refraction can be disregarded. This ascertainment is also made possible through the use of an appropriate sensitivity metric. In this embodiment, in particular, no optical effect with the "determined subjective refraction" needs to be held in order to ascertain the sensitivity. In this embodiment, the subjective refraction result can be taken from a fitted model for the dependence of visual acuity on the preset effect, if applicable.

According to one embodiment, the subjective refraction result is not determined on the basis of, i.e., is determined independently of, an applied correction in the subjective refraction result, but the subjective refraction result is determined from an adapted model for the dependence of the visual acuity on the optical effect of the applied correction. The method can therefore be performed without holding the subjective refraction result. For this purpose, at least three visual acuity values are preferably determined for at least three different corrections, from which the subjective refraction result can be calculated, e.g., by means of a suitable sensitivity metric. In this case, the determination of the subjective refraction result can be shortened, as it does not need to be continued after a sufficient number of determined visual acuity values have been obtained.

According to one embodiment, the determination of the subjective refraction result is performed by means of a refraction unit and/or the visual acuity determination is performed by means of optotypes displayed to the test subject. For example, refraction glasses and/or a phoropter can be used as a refraction unit. The phoropter can be controlled manually, semi-automatically and/or completely automatically by the refractionist. The use of a phoropter in combination with visual tasks based on optotypes displayed to the test subject is particularly preferred here and simplifies the method.

According to one embodiment, the determination of the subjective refraction result, the determination of the first and second visual acuity, and/or the determination of the sensitivity is performed with software support and/or at least partially automatically. Here, visual acuity values with the associated refraction values can be automatically controlled, checked and/or further processed to determine the sensitivity.

According to one embodiment, the first visual acuity and/or the second visual acuity is determined monocularly and/or binocularly. The decision to use monocular and/or binocular visual acuity may depend on the test subject and/or optical corrections to be made.

According to one embodiment, the ascertained sensitivity is used to create at least one individual eyeglass lens for the test subject. The measurement data ascertained can be used to adapt the at least one individual eyeglass lens well to the at least one eye of the user. This applies in particular to the creation of ophthalmic eyeglass lenses.

According to one embodiment, a light field indicator is used for determining the subjective refraction result in order to display at least one test image with simulated wavefronts to the test subject. The simulated wavefronts can correspond to the optical effects, e.g., the first and/or second applied refraction. The light field display can show one or more test images with associated simulated applied refractions simultaneously and/or consecutively as part of the determination of subjective refraction.

By means of the light field indicator, visual symbols (such as optotypes) can be displayed, e.g., in tabular form. For example, a different applied refraction can be simulated for each column (alternatively for each row) and the visual symbols in each row (alternatively in each column) can have a different size (e.g., decreasing downwards or to the right). Then, the test subject can be asked up to which column and/or row they can subjectively recognize and/or read out the visual symbols well. In this way, the visual acuity can be ascertained at the same time as the subjectively best applied refraction. This can allow a quick determination of the subjective refraction result.

Furthermore, the test subject can be asked for two or more columns and/or rows up to which respective row and/or column they can recognize the visual symbols well in each case. This allows visual acuity to be determined for different applied refractions without changing the display and/or in direct comparison.

One aspect relates to a method for determining a sensitivity of at least one eye of a test subject, having a refraction unit for determining a subjective refraction result for the at least one eye of the test subject. A visual acuity determination unit is configured to, while performing the determination of the subjective refraction result, determine a first visual acuity of the at least one eye for a first applied refraction and a second visual acuity of the at least one eye for a second applied refraction. The second applied refraction is different from the first applied refraction. A sensitivity ascertaining unit ascertains the sensitivity of the at least one eye taking into account the first and second visual acuities at the first and second refractions.

The device can be designed as a device system and additionally comprise units; for example, a display unit and/or a control unit. Furthermore, the device and/or the device system can comprise an eyeglass lens data creation unit, which can be integrated into a controller, for example. One or more of these units can be software-controlled. The device can be used to performed the method described above. Therefore, all the explanations on the method also relate to the device and vice versa.

One aspect relates to a computer program product comprising computer-readable program parts which, when loaded and executed, cause a device according to the preceding aspect to perform a method according to the aspect described at the outset, wherein the computer program product at least partially controls and/or regulates at least one of the following units:

the refraction unit;

the visual acuity determination unit;

the sensitivity ascertaining unit;

a controller; and/or an eyeglass lens data creation unit for creating at least one individual eyeglass lens and/or for calculating at least one eyeglass lens surface from the acquired measurement data.

The computer program product can be used for partially automated and/or completely automated sensitivity determination and/or determination of the subjective refraction.

BRIEF DESCRIPTION OF THE DRAWINGS

In the following the invention is explained in more detail with reference to the exemplary embodiments and figures. Individual features of these exemplary embodiments and figures may be combined with other exemplary embodiments. In the figures.

DETAILED DESCRIPTION

Figure 1A:
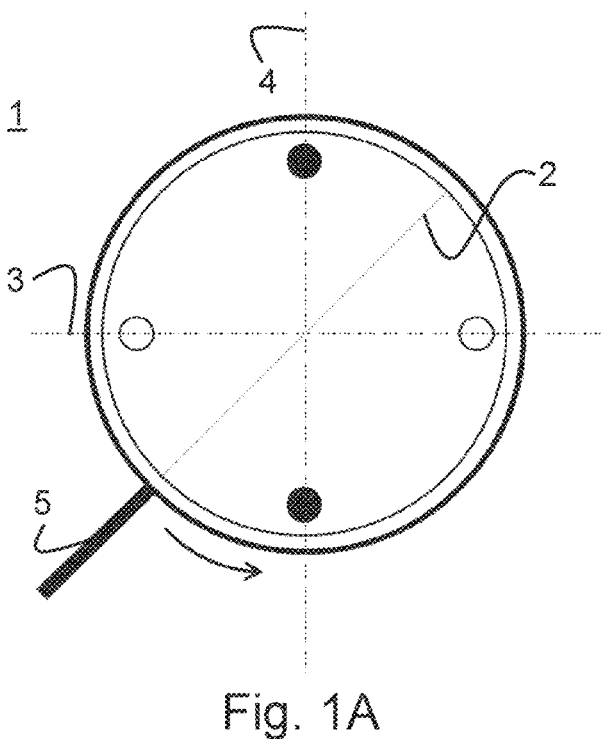
FIG. 1A shows a schematic representation of a cross cylinder in a first position.

In the context of the present invention, the terms "substantially" and/or "about" may be used to include a deviation of up to 5% from a numerical value following the term, a deviation of up to 5° from a direction following the term and/or from an angle following the term.

Terms such as upper, lower, above, below, lateral, etc. refer—unless otherwise specified—to the earth's reference system in an operating position of the subject matter of the invention.

Exemplary Embodiments of a Sensitivity Metric

The sensitivity can be calculated using a metric space in which different refraction values represent individual points. For example, a refraction value can be represented threedimensionally, e.g., with the coordinates s, c, and $\alpha$. Here, s can depend on the strength of a sphere correction and be given, for example, in diopters (which can also be abbreviated to dpt). c can depend on the strength of a cylinder correction and be given, for example, in dpt. $\alpha$ can depend on the axial position of the cylinder correction and be given in degrees, e.g., from 0 to 180°. Alternatively, other coordinates can be used.

In the following, it is assumed by way of example that the best refraction, i.e., the specific subjective refraction result, is denoted in this sensitivity metric by $s_0$, $c_0$, and $\alpha_0$ and the associated visual acuity by $v_0$. When performing the method, at least two visual acuity values are determined. In the general case, in addition to the visual acuity $v_0$ at the subjective refraction at n, further refractions $s_i$, $c_i$, $\alpha_i$ with associated visual acuity $v_i$ with $i \in [1, \ldots, n]$ may have been determined and are thus present.

In a possible sensitivity metric, the distance of a refraction i from the best refraction in the middle sphere $d_i$ and in the cylinder $a_i$ is calculated using equation (1):

$$d_i = \left(s_i + \frac{1}{2} \cdot c_i\right) - \left(s_0 + \frac{1}{2} \cdot c_0\right) \tag{1}$$

$$a_i = \sqrt{c_i^2 + c_0^2 - 2 \cdot c_i \cdot c_0 \cdot \cos(\alpha_i - \alpha_0)}$$

Simple Bilinear Model of a Sensitivity Metric with Knowledge of the Subjective Refraction In one embodiment of a bilinear model of a sensitivity metric, the following relationship shown in equation (2) applies to the dependence of visual acuity for each individual measurement for a refraction i. In a simplified case, it can be assumed that the test subject cannot compensate for fogging by accommodation.

$$\lg v_i = m_d \cdot |d_i| + m_a \cdot a_i + \lg v_0 \tag{2}$$

Here $m_d$ stands for the sensitivity at a spherical distance and $m_a$ stands for the sensitivity at a cylindrical distance. Such a separation between a spherical and a cylindrical misrefraction can be used to account for the fact that test subjects may react very differently to these two components of a misrefraction. In this way, from data from D. Methling: Bestimmung von Sehhilfen [*Determination of Visual Aids*], 2nd ed. Ferdinand Enke Verlag, Stuttgart 1996, it can be determined that, empirically determined, the equations (3) apply approximately to the population average:

$$m_d = \frac{2}{1\ dpt} \cdot \lg\ 0{,}5 = -0{,}601 dpt^{-1} \tag{3}$$

$$m_a = \frac{1}{1\ dpt} \cdot \lg\ 0{,}5 = -0{,}301 dpt^{-1}$$

In general, the preceding equation (2) has three independent parameters $m_a$, $m_d$, $v_0$, Therefore, the system of equations (2) with three measurements i=1, 2, 3 of three visual acuity values $v_1$, $v_2$, $v_3$ at three different refractions ($s_1$, $c_1$, $\alpha_1$; $s_2$, $c_2$, $\alpha_2$; $s_3$, $c_3$, $\alpha_3$) can be uniquely solved with the system of equations (2a):

$$m_a = -\frac{1}{nenner}\left(\log\left(v_1^{|d_2|-|d_3|}\right) + \log\left(v_2^{|d_3|-|d_1|}\right) + \log\left(v_3^{|d_1|-|d_2|}\right)\right) \tag{2a}$$

-continued $$m_d = -\frac{1}{nenner}\left(\log\left(v_1^{a_3-a_2}\right) + \log\left(v_2^{a_1-a_3}\right) + \log\left(v_3^{a_2-a_1}\right)\right)$$

$$\log v_0 = -\frac{1}{nenner}\left(\log\left(v_1^{a_2|d_3|-a_3|d_2|}\right) + \log\left(v_2^{a_3|d_1|-a_1|d_3|}\right) + \log\left(v_3^{a_1|d_2|-a_2|d_1|}\right)\right)$$

$$mit\ nenner = (a_2-a_3)|d_1| + (a_3-a_1)|d_2| + (a_1-a_2)|d_3|$$

Here, in a preferred embodiment, one of the three visual acuity measurements can take place at optimal correction conditions, i.e., at subjective refraction. Thus, e.g., when i=3: $(s_3, c_3, \alpha_3)=(s_0, c_0, \alpha_0)$. In this optimal correction condition, $a_3=a_0=0$ and $d_3=d_0=0$. Thus, the third of the equations (2a) is automatically fulfilled. The other equations then take the following form of the system of equations (4):

$$m_a = -\frac{1}{nenner}\left(|d_2|\log(v_1/v_0) - |d_1|\log(v_2/v_0)\right) \quad (4)$$

$$m_d = -\frac{1}{nenner}\left(-a_2\ \log(v_1/v_0) - a_1\ \log(v_2/v_0)\right)$$

$$mit\ nenner = a_2|d_1| - a_1|d_2|$$

The system of equations (4) thus provides an exemplary embodiment of a simplified bilinear model of a sensitivity metric. The system of equations (4) can be solved with knowledge of the subjective refraction and with knowledge of two additional visual acuity values for two additional refraction values (for i=1,2). Thus, the sensitivity can be determined from the system of equations (4).

If more than two additional visual acuity values are measured in addition to the visual acuity $v_0$ in the subjective refraction, the sensitivity can be ascertained more precisely by determining $m_d$ and $m_a$ from all the data using a balancing method, e.g., the least squares method. Furthermore, outliers can be excluded from the measurement data to increase the quality of the sensitivity determination.

Simplified Linear Model of a Sensitivity Metric with Knowledge of the Subjective Refraction In a further simplified, less custom model of the sensitivity metric, e.g., when there is only one measurement at a misrefraction i=1, a correlation between the spherical and the cylindrical refraction distance can be assumed according to equation (5):

$$m_d=m$$

$$m_a=f \cdot m_d=f \cdot m \quad (5)$$

Here, the parameter f can be derived from empirical values and be a scalar, for example. With the assumption according to equation (5), the system of equations (2) simplifies to the following equation (6):

$$\lg v_i=m \cdot (d_i+f \cdot a_i)+\lg v_0 \quad (6)$$

Thus, the sensitivity m from a measurement at an error refraction i can be ascertained from equation (7):

$$m = \frac{a_i + f \cdot |d_i|}{\lg v_i - \lg v_0} \quad (7)$$

A value for f can be derived from relevant literature, e.g., f=½ can be set, derived from Applegate, R. A, Sarver, E. J, Khemsara, V., Are all aberrations equal?, J Refract Surg.

2002, 18: p556-p562. Or f=1 can be set, derived from Atchison et al. 2009, Blur limits for defocus, astigmatism and trefoil, VisionResearch.

A linear relationship does not necessarily have to be assumed for equation (5). Alternatively, more complex correlations can be established and the sensitivity derived therefrom, e.g., depending on a number of the independent parameters and/or the visual acuity measurements—by inserting them into correspondingly resolved correlations, see equations (4) and (7). Sensitivity can also be derived from an equalization method, such as least squares.

Further Models of a Sensitivity Metric with Knowledge of the Subjective Refraction The sensitivity can also be calculated on the basis of other models. For example, models are known from R. Blendowske, Unaided Visual Acuity and Blur: A Simple Model, Optometry and Vision Science, Vol. 92, No. 6, 2015, which are characterized by particular simplicity and are based on only a few parameters. Such simple models are particularly suitable for calculating sensitivity and for fitting when data is scarce, for example because overfitting can be avoided.

If a larger number of parameters are available individually, a model with many different parameters is more suitable, as described, for example, in DE 10 2017 007 663 A1.

Essentially, a variety of different models can be used. The model used in individual cases may depend on the number of visual acuity values determined for different refractions. With a sufficient number of measured visual acuity values, relatively complex, not necessarily linear models can be set up, the parameters of which can be adjusted to the measurements.

The models listed above as examples can be generalized, e.g., in that a function describing the visual acuity in the power vector space has contours of constant visual acuity that correspond to ellipsoids or ovoids containing the point of maximum visual acuity. This can be analogous to a method presented in A. Rubin and W. F. Harris, Closed Surfaces of Constant Visual Acuity in Symmetric Dioptric Power Space, Optometry and Vision Science, Vol. 78, No. 10, 2001. Axle ratios can differ individually in a range from 0.25 to 4. Instead of individually measured values, mean values, medians or other estimated values of the corresponding model parameters of the population can also be used to calculate visual acuity.

In one exemplary embodiment, a generalization from the above equation (6) leads to different factors f, e.g., to equation (8):

$$\lg v_i = \left\{\left(d_i, a_i^{ort}, a_i^{obl}\right)E \begin{bmatrix} m_1^2 & 0 & 0 \\ 0 & m_2^2 & 0 \\ 0 & 0 & m_3^2 \end{bmatrix} R^T\left(d_i, a_i^{ort}, a_i^{obl}\right)^T\right\}^{1/2} + \lg v_0 \quad (8)$$

Here, $$a_i^{ort}$$

and $$a_i^{ort}$$

denote the astigmatism of the misrefraction with orthogonal (J0) and oblique (J45) axis positions, respectively, and are defined as:

$$a_i^{ort} = -\frac{c_i}{2}\cos(2\alpha_i) + \frac{c_0}{2}\cos(2\alpha_0) \text{ and}$$

$$a_i^{obl} = -\frac{c_i}{2}\sin(2\alpha_i) + \frac{c_0}{2}\sin(2\alpha_0).$$

R represents a rotation matrix that determines an orientation of an ellipsoid of constant visual acuity in the power vector space of vectors $$\left(d_i, a_i^{ort}, a_i^{obl}\right).$$

The eigenvalues $m_1$, $m_2$, $m_3$ denote the sensitivities to fogging in the direction of the first, second and third column vectors of the rotation matrix R in the power vector space.

Exemplary Embodiments of Models of a Sensitivity Metric without Knowledge of the Subjective Refraction In some exemplary embodiments, the sensitivity can be determined without determining the subjective refraction. This can be done when a visual acuity measurement is taken for several different refractions. In this case, the best refraction, i.e., the subjective refraction, can be ascertained from the measurement data obtained in the process. Furthermore, an actually ascertained best subjective refraction can be checked from the measurement data by means of a model of a sensitivity metric.

It can be assumed that a fogging, i.e., an intentional misrefraction towards minus, can be compensated for by the test subject by accommodation of at least one eye. In this case, a point can be selected in the linear model according to the preceding equations (2) and (6) at which the visual acuity curve bends. For non-linear models where saturation occurs, the best refraction can be calculated directly as a parameter of the system of equations. For this purpose, in the corresponding formulae, i.e., in particular already in equation (1), the misrefraction, i.e., the distances $d_i$ and $a_i$, must be replaced by the difference between best refraction and correction in the visual acuity measurement.

Exemplary Embodiment of a Method for Determining the Subjective Refraction by Ascertaining Visual Acuity Values In an exemplary embodiment, an objective refraction is first determined for a test subject, i.e., refraction values are ascertained on the basis of an objective measurement. For example, a method for determining such objective parameters is known from DE 10 2011 120 973 A1. The objective parameters can comprise aberrometric measurement data and/or pupillometric measurement data. The objectively ascertained measurement data, i.e., the aberrometric measurement data and/or the pupillometric measurement data, can be used to calculate an objectively optimized refraction.

A determination of the best subjective refraction, i.e., the subjective refraction result, can essentially be made by means of a method described in the prior art, see e.g., D.

Methling: Bestimmung von Sehhilfen [*Determination of Visual Aids*], 2nd ed. Ferdinand Enke Verlag, Stuttgart (1996).

As a starting point for determining the subjective refraction result, the objectively ascertained refraction values can be used, which are fogged by a predetermined distance, e.g., by an additional sphere of 0.50 to 1.00 dpt. The refraction values fogged in this way can be used as starting refraction values.

Instead of the objectively ascertained refraction values, other refraction values can be used as starting refraction values, e.g., the values of an already existing old correction device, e.g., an older pair of glasses. Alternatively, any refraction values and thus any optical effects held in reserve can be used as starting refraction values.

Subsequently, the following four main method steps a) to d), supplemented by method step e) if necessary, are carried out when determining the test subject's subjective refraction. In the case of a monocular determination of the subjective refraction, only method step a) or b) can alternatively be carried out, optionally supplemented by method step e):

a) Monocular determination of the most positive spherical-cylindrical refraction at which subjectively the best visual acuity is produced for a first eye of the test subject, e.g., for the right eye;

b) Monocular determination of the most positive spherical-cylindrical refraction at which subjectively the best visual acuity is produced for a second eye of the test subject, e.g., for the left eye;

c) Adjustment of binocular accommodative balance;

d) Binocular determination of the most positive spherical-cylindrical refraction at which subjectively the best visual acuity is produced for both eyes of the test subject; and e) Subjective evaluation of the refraction values ascertained in this way in a test frame.

These steps follow a logical pattern based on visual acuity measurements. A change in the strength of the sphere correction is preferably only made if the addition of a sphere of −0.25 dpt improves the visual acuity by one line, i.e., causes a change of −0.1 log MAR. This condition can be used throughout as a criterion of change in the addition of a negative sphere.

With a change towards a positive spherical effect, i.e., with the addition of a sphere of +0.25 dpt, the visual acuity must improve or remain the same. This condition can be used throughout as a criterion of change in the addition of a positive sphere.

These different criteria result from the fact that one you be on a plateau when adding a positive sphere. For example, if you start with +3.00 dpt and the refraction you actually need is, say, +3.25 dpt, your visual acuity will not change, whether you add +0.25 dpt or −0.25 dpt. Therefore, the addition of a positive sphere is subject to the further criterion of change that also applies to a visual acuity that remains the same.

A line of visual acuity can be considered to have been reached when the test subject can recognize at least 60% of the optotypes displayed on this line.

In the monocular determination of the refraction for the first eye, i.e., in method step a), a strength of the required sphere correction of the subjective refraction can first be determined. The second eye can be covered, e.g., the left eye. The first eye is presented with the measured starting refraction for the right eye. If a visual acuity determination for the starting refraction gives a visual acuity value of 0.1 log MAR or better, a first positive lens for the first eye can be added to the starting refraction. Then, the visual acuity is measured again. If the respective change criterion is reached, another positive lens will be added until the applicable change criterion is no longer reached. If the applicable change criterion is no longer achieved, the refractionist can add a negative lens instead. If the change criterion is reached, another negative lens can be added until the change criterion is no longer reached.

This completes the determination of the strength of sphere correction required and is followed by a determination of an axis and/or axis position of any cylinder correction required.

Figure 1B:
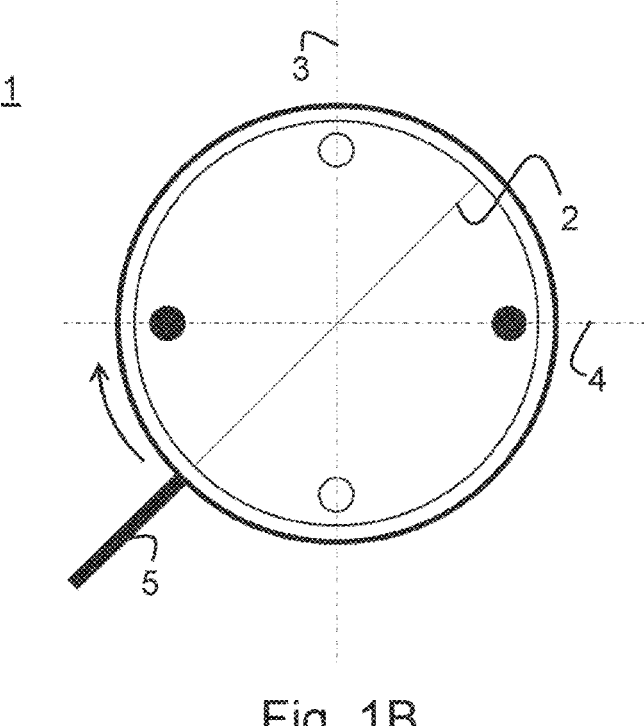
FIG. 1B shows a schematic representation of a cross cylinder in a second position.

For this purpose, a refractionist can use a cross cylinder 1 to determine an axis of any astigmatism present in the first eye. FIGS. 1A and 1B show a schematic representation of such a cross cylinder 1, which is also known as a Jackson cross cylinder. The cross cylinder 1 has a handle 5, through which a handle axis 2 runs. The cross cylinder 1 is an optical aid and has two cylinders crossed at 90°, namely a plus cylinder and a minus cylinder. The handle axis 2 is arranged at 45° to a cylinder axis 3 of the plus cylinder and at 45° to a cylinder axis 4 of the minus cylinder.

The test subject may be shown optotypes indicating worst visual acuity of at least 0.2 log MAR. The handle axis 2 of the cross cylinder 1 can be arranged on a suspected and/or the objectively ascertained axis of an astigmatism of the test subject's first eye. The cross cylinder 1 can then be turned over between the two positions shown in FIGS. 1A and 1B, wherein the handle axis 2 remains true to position. The test subject can be asked which of these two rotational positions of the cross cylinder 1 produces a better visual experience. If the test subject does not notice any difference, the axis for the refraction of the first eye has been found and the determination of the required cylinder strength is continued, see below. If the test subject prefers one of the two rotational positions shown in FIGS. 1A and 1B, the handle axis 2 can be shifted clockwise exactly when the cylinder axis 4 of the minus cylinder is in the preferred rotational position clockwise from the handle axis 2, see situation in FIG. 1B. The handle axis 2 can be shifted anti-clockwise exactly when the cylinder axis 4 of the minus cylinder is in the preferred anti-clockwise rotation position from the handle axis 2, see situation in FIG. 1B.

This check with the two rotation positions and the twisting of the handle axis 2 can be repeated until the test subject no longer recognizes a difference between the two rotation positions, or until the handle axis 2 is moved back and forth in the process. In the latter case, the axis that most closely matches an older axis can be selected from these most recently used axis positions, e.g., an axis for this first eye that was used in an older pair of the test subject's eyeglasses. Alternatively, the axis that is closer to a non-slanted astigmatism can be selected from these most recently used axis positions.

This completes the determination of the axis of the required cylinder correction and is followed by a determination of a strength of the required cylinder correction.

The cross cylinder 1 can be arranged for this purpose in such a way that its cylinder axis 3 of the plus cylinder and its cylinder axis 4 of the minus cylinder are arranged exactly on the corresponding cylinder axes of the objectively determined refraction that is already held out to the first eye of the test subject. The cross cylinder 1 can be turned over in the same way as for the determination of the axis position described above, i.e., with the handle axis 2 in the correct position. If a rotation position preferred by the test subject is the rotation position where the two cylinder axes of the minus cylinders overlap, a negative cylinder strength can be added, e.g., −0.25 dpt. If the rotation position preferred by the test subject is the one in which the cylinder axis 4 of the plus cylinder of the cross cylinder 1 overlaps the cylinder axis of the minus cylinder of the refraction held in front, a negative cylinder strength can be subtracted, also e.g., in steps of quarter diopters. The refractionist can repeat this until the test subject no longer prefers any of the rotational positions, or until the strength of the cylinder correction changes back and forth in the process. In the latter case, the lowest strength of cylinder correction used should be selected.

When determining the strength of the required cylinder correction, care can be taken to ensure that the previously determined strength of the required sphere correction remains the same. This means, for example, that for every 0.50 dpt change in the strength of the cylinder correction, the strength of the sphere correction is also changed by 0.25 dpt in the other direction.

After determining both the strength and the axis of the required cylinder correction, the sphere correction can be checked again. This can be done in the same way as described above in connection with determining the strength of the required sphere correction. Optionally, if the strength changes significantly, the axis determination can be repeated to achieve a more reliable result.

This completes a monocular determination of the subjective refraction for the first eye, which consists of the determined strength of the required sphere correction and the determined strength and axis of the required cylinder correction.

The refraction for the second eye is then determined, i.e., method step b). This is done in exactly the same way as method step a), only for the second eye and with the first eye covered.

As a result, the monocular subjective refraction for the second eye is determined, which consists of a certain strength of a required sphere correction and a certain strength and axis of a required cylinder correction.

The binocular accommodative balance is adjusted in method step c). To do this, both eyes are uncovered. Fogging can be added to each of the two monocular subjective refractions for the first and second eye, e.g., a fogging of +0.50 dpt each. In addition, a separator can be used, e.g., a polarization filter and/or a red/green filter. One goal may be for both eyes to enter the same accommodation state. The separator can allow the test subject to see different display parts of a target display with each of their eyes and compare their sharpness. For this purpose, in addition to the display parts that can only be perceived by one eye at a time, a common display part of the target display should be visible to both eyes. Only then can a meaningful fusion take place and the visual acuity be checked. If one of the two eyes sees sharper than the other, the refraction of that eye can be further fogged with a positive sphere. The refractionist may repeat this procedure until both parts of the target display appear to the subject to be approximately equally sharp, or until the slightest difference in sharpness is perceived.

For method step d), i.e., for binocular determination of the most positive spherical-cylindrical refraction at which subjectively the best visual acuity is produced for both eyes of the test subject, the separator is first removed. A visual acuity determination is then performed. For binocular determination of the strength of sphere correction required, the same procedure as in steps a) and b) can be followed, only here for both eyes at the same time. The two monocular cylindrical refractions already determined can remain unchanged here. The result can be used as the binocular subjective refraction. Alternatively, the binocular subjective refraction can be determined as the result of supplementary step e).

This is followed by method step e), in which a subjective evaluation of the refraction values contained after method step d) is carried out in a test frame. For this purpose, the refraction values determined in method step d) are placed in a test frame and adapted to the test subject's face. For this purpose, the test subject's pupils in particular can be centered in the middle of test lenses with these refraction values. A test lens check can be performed in an open outdoor environment, wherein the test subject can fix a target in the distance.

The refractionist can add a sphere strength of +0.25 dpt binocularly and ask the test subject whether the visual impression appears better or remains the same with or without this addition. If the visual impression appears better or remains the same due to this addition, the refraction values ascertained in method step d) are used as the finally determined subjective refraction values, which are supplemented by this binocular addition of +0.25 dpt in the sphere.

If the addition does not improve or at least leave the visual impression the same, the sphere strength can be changed binocularly by −0.25 dpt and the test subject asked whether the visual impression appears better with or without this reduction by a quarter of a diopter. If this change to the negative leads to a better visual impression, the sphere strength can be changed again binocularly by −0.25 dpt. The test subject can be asked whether the visual impression appears better with a change of −0.25 dpt or of −0.50 dpt. If the −0.25 dpt change results in a better visual impression, the refraction values determined in method step d) are used as the final subjective refraction values, to which the −0.25 dpt binocular change in the sphere is added. If the −0.50 dpt change results in a better visual impression, the refraction values determined in method step d) are used as the final subjective refraction values, to which the −0.50 dpt binocular change in the sphere is added.

This concludes the determination of binocular subjective refraction for the test subject.

During this determination of binocular subjective refraction, visual acuity is measured during at least two different upstream refractions. At least a first visual acuity at a first refraction and a second visual acuity at a second refraction are measured. For example, the visual acuity can be determined in particular at the best correction, i.e., at the refraction values determined at the end of method step d). In addition, the visual acuity can be determined with a different correction, preferably with a more positive correction. This can be advantageous because more minus can possibly be compensated for by accommodation. Preferably, the two corrections at which the two visual acuity values are determined differ from each other from about 0.50 dpt to about 1.25 dpt in the sphere.

Visual acuity can be measured with a cylindrical correction that deviates from the determined subjective refraction. Jackson cross cylinders can be used for this purpose, e.g., with plus/minus 0.50 dpt, or a plus cylinder with e.g., +1.00 dpt compared to the determined subjective refraction.

The strength of the deviation of the correction from the optimum correction can also depend on the amount of addition or be roughly based on the maximum values of the unwanted astigmatism expected with a progressive lens. The visual acuity of a test subject with a lower addition would therefore be measured with less spherical or cylindrical fogging than the visual acuity of a test subject with a higher addition.

Visual acuity can be determined by means of optotypes, wherein visual acuity is considered to be achieved when at least 60% of the optotypes of a corresponding line have been recognized.

The visual acuity can be measured during and/or after the method step(s) a), b), c) and/or d) and stored and/or written down for a subsequent calculation of the sensitivity. For example, at least two binocular visual acuity values can be determined during method step c) and/or d). One or more monocular visual acuity values can be determined during method steps a) and/or b).

The visual acuity can be determined monocularly, in particular during method steps a) and/or b). For this purpose, preferred times of the method steps a) and b) at which a visual acuity determination is advantageous are listed below.

The visual acuity can be measured in particular at the beginning of the determination of the subjective refraction, e.g., at the beginning of the method steps a) and/or b), since the refraction applied first usually still has a relatively large distance from the subjective refraction result. A sufficient distance between the first and second applied refraction usually leads to a reliable determination of the sensitivity.

Visual acuity can be determined during the sphere adjustment and/or after the sphere has been ascertained. The refraction applied when the visual acuity is ascertained afterwards is usually very different from the refraction applied at the beginning. Therefore, for example, a monocular visual acuity can be determined with the refraction applied first and last (in method step a) and/or in method step b)).

The visual acuity can be determined before determining the axial position of the cylinder correction, in particular exactly when checking whether a cylinder correction is necessary at all. This can be done in method step a) and/or b).

Visual acuity can be determined during the alignment of the axis and/or after the axis has been ascertained. For example, the visual acuity can be determined when the cross cylinder is in one position, or when the positions of the cross cylinder are twisted against each other. If the visual acuity is determined with the positions of the cross cylinder twisted against each other, an astigmatic difference is guaranteed to be assigned to the visual acuity values, which in turn can lead to a reliable determination of the sensitivity.

Visual acuity can be determined during the alignment of the cylinder strength and/or after the cylinder strength has been ascertained.

Analogous to the above examples, when the visual acuity can be determined during method steps a) and b), the visual acuity can also be determined binocularly during method steps c) and d). In particular, it can be determined at the very beginning of method steps c) and/or d) and/or at the very end of these method steps.

Preferably, visual acuity is determined more than twice, i.e., at least three times or even at least four times. The number of visual acuity measurements increases the accuracy of the sensitivity determination. The number of visual acuity measurements can increase the accuracy, in particular when the assigned applied refractions differ only slightly from each other.

Therefore, in one embodiment, it is possible to check, for example, how much the first and second applied refraction differ from each other. If the difference is too small, the visual acuity is determined at least a third time for a third applied refraction that differs from both the first and the second.

In general, an image can always be displayed as a test image, i.e., for each applied refraction, on the basis of which the visual acuity can be determined. For example, different sized visual symbols such as optotypes can be displayed in different columns and/or rows on the test image. The test subject can be asked to indicate up to which column and/or row they can recognize the optotypes well. This can result in a relatively large number of specific visual acuities for an equally large number of different applied refractions. This in turn can lead to a more accurate evaluation using sensitivity metrics and thus to a reliably determined sensitivity.

In general, visual acuity can also be determined in other systems, e.g., by determining J0 and J45 and/or Harris vectors instead of axis and cylinder strength. This technique is known, for example, from the paper "Closed Surfaces of Constant Visual Acuity in Symmetric Dioptric Power Space" by Alan Rubin et al, Optometry and Vision Science, Vol. 78, No. 10, October 2001. This can be used in particular when adaptive lenses are used.

The visual acuity measurement can be used as a control of the specific subjective refraction.

This means that the test subjects may or may not achieve a given visual acuity. The visual acuity measurement can also be used to obtain information about the behavior of the test subject's visual system.

There are a number of options for measuring visual acuity. Visual acuity can be measured, for example, by means of optotypes, i.e., letters, Landolt rings and/or similar. It can be tested whether the test subject can recognize the optotypes and/or their orientation completely or partially.

Since this may involve a threshold evaluation, it should be ensured that there is no random recognition of the optotypes. This can be achieved by repeating visual tasks. A correct recognition of 60% of the optotypes of a set can be considered as a successful recognition of this set.

Furthermore, a psychophysical assessment of visual acuity can be performed. Such a psychophysical assessment can be based on a display of a sequence of optotypes of different sizes, the recognition of which indicates different visual acuities. This sequence can be changed depending on the test subject's answers. The aim of the assessment may be to converge the sequence of optotypes towards the visual acuity of the test subject, which is used as a threshold for the assessment. The variations of the sequences can be changed depending on the responses of the test subject and the method used.

To assist an algorithm used in this process to converge to the correct visual acuity, the test subject can be asked for the smallest line of optotypes that they can recognize. Then, depending on the output, it can be checked whether the test subject can actually recognize the selected line and/or a smaller one.

Visual acuity can be determined monocularly and/or binocularly. These are different visual parameters that can all be used to calculate eyeglass lenses.

The methods described above for determining visual acuity can be used to check for contrast sensitivity. Target displays can be shown with different and/or the same contrasts. The contrast can be included as a parameter in the sensitivity metric used and thus taken into account. This means that the method can also be used to determine contrast sensitivity, if necessary.

Psychophysical assessment of visual acuity can also be made using sharpness and/or contrast. In this way, the visual acuity can be determined using different sizes of recognizable optotypes, for example, with different contrasts.

Performing a Method for Determining the Subjective Refraction by Ascertaining Visual Acuity Values The method for determining the sensitivity during the determination of the subjective refraction, in particular the exemplary embodiment described above, can be performed e.g., manually by means of measuring glasses and/or a phoropter. In doing so, a refractionist may perform the normal subjective refraction, acquiring the visual acuity achieved during the respective intermediate corrections used one or more times before achieving the best refraction.

The method can be carried out in the context of a guided implementation. In this process, a refractionist is guided through the determination of the refraction by a computer program, for example. For this purpose, the refraction procedure may be implemented on a computer system that prompts the refractionist to adjust a phoropter unit and/or a display unit according to a specification of an algorithm. Feedback from the test subject can be entered and/or automatically acquired, e.g., by means of speech recognition.

The method can be carried out at least partially automatically, i.e., without automatic and/or instrumental detection of feedback from the test subject. A computer system that communicates with a phoropter unit and/or a display unit can also be used for this purpose. The computer system acts as a kind of control unit that controls and/or regulates the phoropter unit and/or the display unit according to the method procedure. A refractionist can thereby adjust the phoropter and/or the display unit, provided that one of these units and/or a function of these units is not controlled by the computer system. The refractionist can enter feedback from the test subject into the computer system.

Alternatively, the method can be performed at least partially automatically with automated collection of feedback from the test subject. Feedback from the test subject can be acquired, e.g., by means of buttons, voice recording and/or eye tracking. In this way, the method procedure, e.g., the execution of method steps a) to e), can be completely automated, in particular since the refractionist does not have to pass on the test subject's feedback to the computer system. A phoropter unit can be used for this purpose, which can communicate with the computer system. A display unit used for this purpose can either show a fixed representation with which visual acuity can be determined, e.g., a classic vision panel with symbols in different sizes, or it can also communicate with the computer system and be designed as a display, for example.

Although an essential aspect of the invention is the acquisition of visual acuity before the best refraction is achieved, in some cases visual acuity (e.g., additional visual acuity) can also be acquired downstream, e.g., for defined fogged conditions after the best refraction has been determined. This is particularly true if the distance between the first and second refraction falls below a minimum distance.

This can also be done, in particular, if the method is carried out by means of a computer program product and/or a device having a control unit, a phoropter unit, a display unit and/or an eye tracking unit. In these cases, the subjective refraction and/or sensitivity can be guided or at least partially ascertained automatically.

At least one visual acuity value can be ascertained after the determination of the best refraction. For this purpose, after the best refraction has been achieved, the visual acuity for the best refraction can be measured first, and then the visual acuity for a fogging of, for example, +2 dpt spherical and/or −2 dpt cylindrical.

In one embodiment, it can be taken into account that too negative a spherical effect of a correction can be accommodated away by the test subject, if necessary. To avoid this, the applied refractions can preferably have more plus than the (expected) refraction result when determining the visual acuity. This can be taken into account while performing the determination of the subjective refraction result.

When using cylinder corrections with a main cut without effect, it can be taken into account that a correction with a given cylinder (of e.g., +1 dpt) and a main cut without effect has an average spherical effect of half the cylinder, i.e., +0.5 dpt in the example. This can be taken into account when calculating a distance between applied refractions. If corrections with a negative cylinder, e.g., −1 dpt, and a main cut without effect are used, an associated negative mean spherical effect is also half the cylinder correction, as −0.5 dpt in the example. If necessary, this negative correction can be compensated for by the test subject through accommodation and then no longer needs to be taken into account. This may be a preferred exemplary embodiment for non-presbyopic test subjects, for example. Corrections such as trial lenses with cylindrical effect without medium spherical effect can avoid this effect. However, they are relatively complex to manufacture, as a positive and a negative main cut are required in each case.

Figure 2:
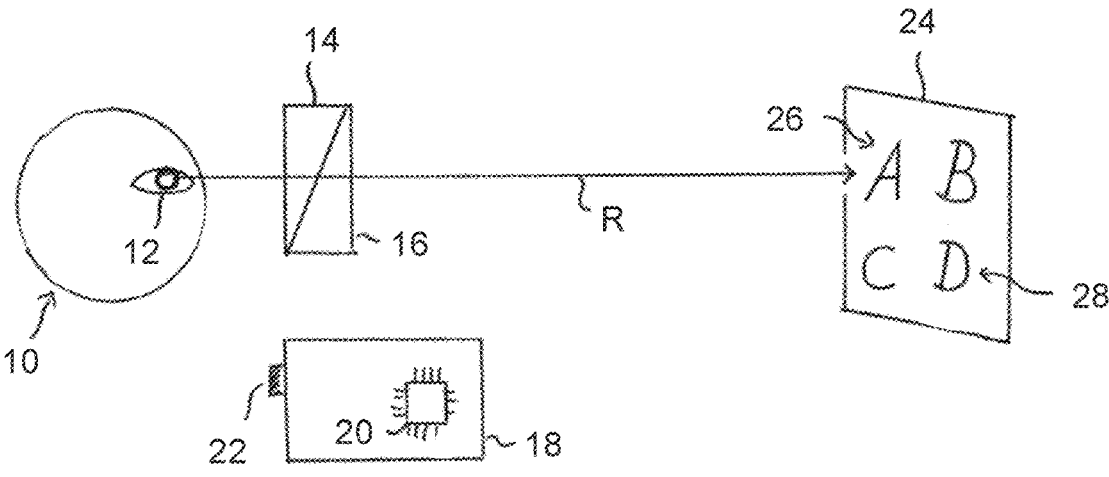
FIG. 2 shows a schematic representation of a first embodiment of a device for determining a sensitivity of at least one eye of a test subject in a first display state.

FIG. 2 shows a schematic representation of a first embodiment of a device for determining a sensitivity of at least one eye 12 of a test subject 10 in a first display state.

The device has a refraction unit 14 for adjusting an applied optical refraction and/or correction for at least one eye 12 of the test subject 10. The refraction unit 14 can, for example, be designed as a phoropter and/or have a phoropter. The device can further have an eye tracking unit 16, which can be arranged, for example, on the refraction unit 14, and which is designed and/or configured to detect a viewing direction R and/or an orientation of the at least one eye 12 of the test subject 10, in particular while the test subject 10 is viewing a displayed test image. This test image can be displayed on a display unit 24 and can comprise a plurality of visual symbols 26 and 28 as optotypes. The visual symbols 26 and 28 can be displayed in test image regions, e.g., one visual symbol 26, 28 in each test image region. To this end, each visual symbol 26, 28 can be displayed with an associated optical correction and/or associated applied refraction.

In the exemplary embodiment shown, the test subject 10 looks with their eye 12 through the refraction unit 14 along the viewing direction R at the visual symbol 26, which is shown in FIG. 2 as an "A". In doing so, the eye tracking unit 16 can detect the viewing direction R. The viewing direction R detected in this way can be used to check that the test subject 10 is looking at the viewed visual symbol 26 and not at one of the unviewed visual symbols 28, which are shown as "B", "C" and "D" in FIG. 2. This makes it possible to distinguish which of the visual symbols 26, 28 the test subject is looking at.

Furthermore, the device can comprise a control unit 18, which can comprise a controller 20 of the refraction unit 14 and/or the display unit 24. The control unit 18 may further be designed and/or configured to read and/or receive the viewing direction R detected by the eye tracking unit 16.

The device can further comprise a trigger 22, which can, for example, be formed on the control unit 18, e.g., as a button. The control unit 18 can be designed and/or configured to read and/or received generated signals from the trigger 22.

The control unit 18 can be designed and/or configured to evaluated generated signals from the refraction unit 14 and/or the display unit 24 and/or the eye tracking unit 16 and/or the trigger 22.

The control unit 18 can further be designed as a signal unit that generates an eye signal containing information on the detected viewing direction R and/or orientation of the at least one eye 12 of the test subject 10. The control unit 18 can be designed as an evaluation unit that determines the optometric parameters of the test subject 10 by evaluating the eye signal as a function of the displayed test image.

The control unit 18 can further be configured as a visual acuity determination unit configured to determine a first visual acuity of the at least one eye 12 for a first applied refraction and a second visual acuity of the at least one eye 12 for a second applied refraction when performing the determination of the subjective refraction result, wherein the second applied refraction is different from the first applied refraction.

The control unit 18 can also be designed as a sensitivity ascertaining unit that ascertains the sensitivity of the at least one eye 12 taking into account the first and second visual acuities at the first and second refractions.

Figure 3:
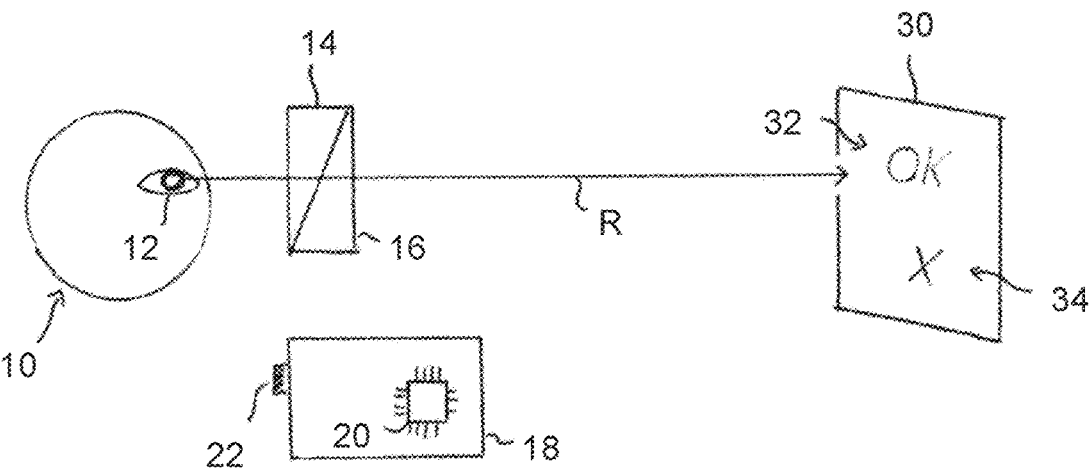
FIG. 3 shows a schematic representation of a second embodiment of a device for determining a sensitivity of at least one eye of a test subject in a second display state.

FIG. 3 shows a schematic representation of a second embodiment of a device for determining the sensitivity of a test subject 10 in a second display state. This device is similar or identical to the device shown in FIG. 2, wherein identical reference numerals indicate identical or similar features. In this regard, the control unit 18 can be adapted and/or configured to additionally evaluate generated signals from a display unit 30, and the controller 20 can comprise a controller of the display unit 30. The display unit 30 of this device can be identical to the display unit 24 of the device shown in FIG. 2.

The device has the display unit 30 on which at least one confirmation field 32 and/or at least one cancellation field 34 can be displayed. Such confirmation and/or cancellation fields 32 and 34 may also be additionally displayed and/or provided in the visual signs 26, 28 shown in FIG. 2. The confirmation field 32 and/or the cancellation field 34 can be designed as an actuation field by means of which the test subject 10 can give feedback to the device.

For example, the test subject 10 can be asked whether their viewing direction R was correctly acquired. This can be done via an audio signal or, for example, via a corresponding display on the display unit 30 and/or 24. If the viewing direction R has been correctly detected, e.g., in that the test subject 10 has just looked at the visual symbol 26 (e.g., "A"), the test subject 10 can fix the confirmation field 32 if this is correct. If the viewing direction R was not correctly detected, the test subject 10 can fix one of the cancellation fields 34. Fixing the confirmation and/or cancellation field 32, 34 can be detected by the eye tracking unit 16 and evaluated by the control unit 18.

Figure 4:
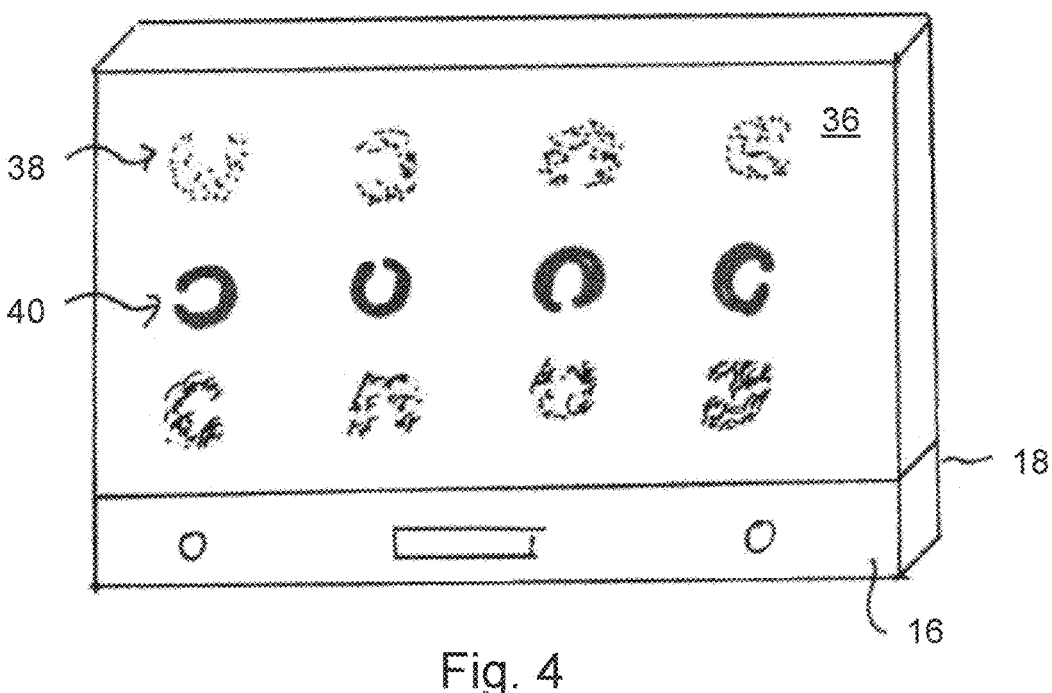
FIG. 4 shows a schematic representation of a light field display of a device for determining a sensitivity.

FIG. 4 shows a schematic representation of a light field display 36 and/or light field indicator of a device for determining the sensitivity of a test subject. The light field display 36 can be used as a refraction unit and/or a display unit. The device has an eye tracking unit 16, which can be integrated into the light field display 36, for example, and/or be connected thereto. Similarly or identically to the embodiments shown in FIGS. 2 and 3, the device has a control unit 18, which can be configured to control the light field display 36 and/or the eye tracking unit 16. The control unit 18 can be designed and/or configured to acquire and/or evaluate generated signals from the light field display 36 and/or the eye tracking unit 16.

A test image is shown on the light field display 36, which is used to determine the subjective refraction of the test subject 10 and has a plurality of test image regions. Here, at least one visual symbol 38, 40 can be displayed in each test image region, for example, which are projected in rows with the same optical correction and/or effect and/or refraction. For each of the test image regions, an associated optical refraction may be simulated for the at least one eye 12 of the test subject 10 such that the impression is created that the at least one eye 12 is viewing the respective visual symbol 38, 40 through the respective associated optical refraction. Here, at least two of the simulated, assigned optical refractions can differ from each other with regard to their optical effect. The test image regions are displayed simultaneously with the assigned optical refractions.

In this case, the visual symbols 38, 40 of each row can be projected with the same optical refraction (within the row). The optical refractions used to project the visual symbols 38, 40 of the individual rows differ from each other, e.g., in the defocus component used. By means of these different defocus components, the subjectively required middle sphere can be determined.

Alternatively, the optical refraction of each row may also differ the sphere effect, the cylinder effect and/or the axis from each other. For example, the optical refraction may differ by a fixed or variable amount, e.g., ¼ diopter each in the sphere and/or cylinder. The refractions can be projected per row rotated against each other around a certain cylinder axis, e.g., 45° each.

In this way, the choice of the subjectively best optical refraction can be made with certainty, since a plurality of visual symbols 38, 40 are provided for each optical refraction, namely a whole series of visual symbols with the same optical refraction. The test subject 10 can thus select the row that is projected with the subjectively best optical refraction for the test subject 10. This allows a more reliable determination of the visual acuity for each refraction used, if desired.

Figure 5:
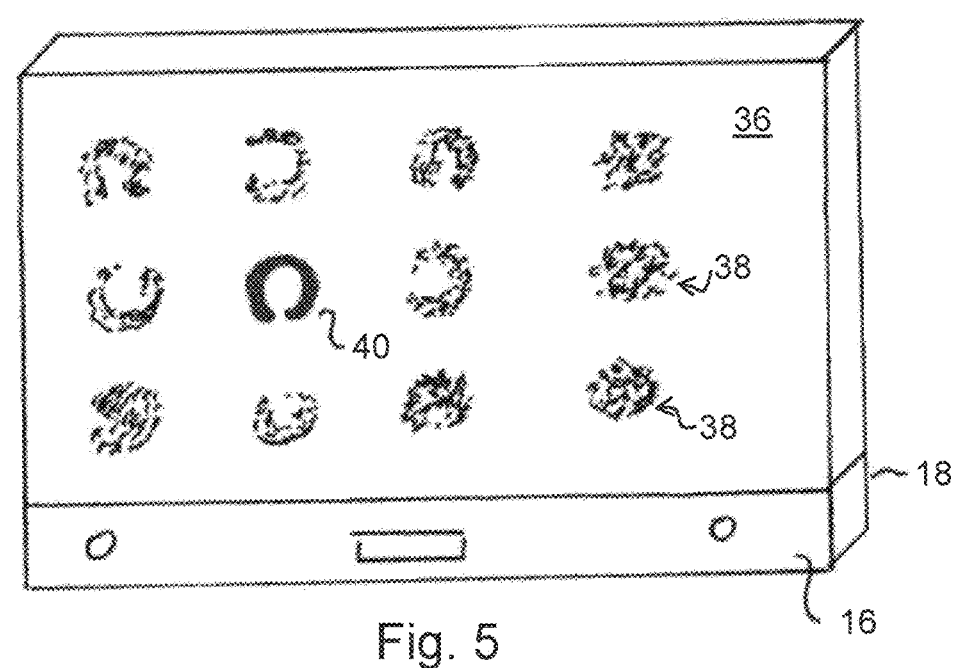
FIG. 5 shows a schematic representation of a light field display of a device for determining a sensitivity.

FIG. 5 shows, similarly to FIG. 4, a schematic representation of a light field display 36 as a light field indicator of a device for determining a sensitivity of a test subject. Here, identical reference numerals indicate identical or similar features.

On the light field display 36, visual symbols 38, 40 are displayed in rows and columns, which can each be projected with different optical refractions. Within each row (or alternatively column), the visual symbols 38, 40 can be projected with equal astigmatism components J0 of the optical correction. However, the astigmatism components J0 of the optical correction of the individual rows (or alternatively columns) differ from each other. On the other hand, within each column (or alternatively row), the visual symbols 38, 40 are projected, each with the same astigmatism component J45 of the optical correction. However, the astigmatism components J45 of the optical correction of the individual columns (or alternatively rows) differ from each other.

For example, the approach shown schematically in FIG. 4 can first be used to determine the defocus component and thus the central sphere. Subsequently, the astigmatism components J0 and J45 can be determined, for example, using the approach shown schematically in FIG. 5. Together, this results in the sphere, cylinder and axis of the subjectively required optical refraction.

LIST OF REFERENCE NUMERALS

1 Cross cylinder
2 Handle axis
3 Cylinder axis of the plus cylinder
4 Cylinder axis of the minus cylinder
5 Handle
10 Test subject
12 Eye
14 Refraction unit
16 Eye tracking unit
18 Control unit
20 Controller
22 Trigger
24 Display unit
26 Viewed visual symbol
28 Unviewed visual symbol
30 Display unit
32 Confirmation field
34 Cancellation field
36 Light field display
38 Visual symbol
40 Visual symbol
R Viewing direction

The invention claimed is:

1. A method for determining a sensitivity of at least one eye of a test subject, comprising:
   determining a subjective refraction result for the at least one eye of the test subject;
   while determining the subjective refraction result, determining a first visual acuity of the at least one eye for a first applied refraction;
   while determining the subjective refraction result, determining a second visual acuity of the at least one eye for a second applied refraction, wherein the second applied refraction is different from the first applied refraction; and
   ascertaining the sensitivity of the at least one eye, taking into account the first and second visual acuities at the first and second applied refractions.

2. The method according to claim 1, wherein at least the first visual acuity is determined before the subjective refraction result for the at least one eye is determined.

3. The method according to claim 2, wherein the determined subjective refraction result is used as the second applied refraction and the second visual acuity is determined for the determined subjective refraction result.

4. The method according to claim 1, wherein the sensitivity of the at least one eye is ascertained on the basis of a sensitivity metric, and this ascertainment of the sensitivity is carried out from visual acuity measurements at applied refraction values which do not have a distance from one another and/or from the refraction result which distance is specifically predetermined and/or optimized for ascertaining the sensitivity.

5. The method according to claim 1, wherein for determining the subjective refraction result, different optotypes are displayed, and while determining the subjective refraction result, a visual acuity belonging to the displayed optotypes is determined as the first and/or second visual acuity.

6. The method according to claim 1, wherein the first applied refraction has a distance from the second applied refraction of at least half a diopter in the sphere and/or of at least one diopter of a cylinder.

7. The method according to claim 1, wherein after determining the subjective refraction result, it is checked whether the first applied refraction has a predetermined spherical and/or cylindrical minimum distance from the second applied refraction, and in the event that this predetermined minimum distance is not reached, a third visual acuity for a third applied refraction is determined which is spaced apart from the first and/or second applied refraction at least by the predetermined minimum distance, and the sensitivity of the at least one eye is ascertained taking into account the third visual acuity at the third applied refraction.

8. The method according to claim 1, wherein the sensitivity of the at least one eye is ascertained on the basis of a linear model in which a dependence of the sensitivity for a cylindrical refraction distance on the sensitivity for a spherical refraction distance is assumed.

9. The method according to claim 1, wherein a third visual acuity of the at least one eye for a third applied refraction is determined, and wherein the sensitivity of the at least one eye is ascertained taking into account the first, second and third visual acuities at the first, second and third applied refractions on the basis of a bilinear model.

10. The method according to claim 1, wherein the sensitivity is ascertained without taking into account the determined subjective refraction result.

11. The method according to claim 1, wherein the determination of the subjective refraction result is performed by means of a refraction unit and/or the visual acuity determination is performed by means of optotypes displayed to the test subject.

12. The method according to claim 1, wherein the determination of the subjective refraction result, the determination of the first and second visual acuity, and/or the determination of the sensitivity is performed with software support and/or at least partially automatically.

13. The method according to claim 1, wherein the first visual acuity and/or the second visual acuity is determined monocularly and/or binocularly.

14. The method according to claim 1, wherein the ascertained sensitivity is used to create at least one individual eyeglass lens for the test subject.

15. A device for determining a sensitivity of at least one eye of a test subject comprising:

a refraction unit configured to determine a subjective refraction result for the at least one eye of the test subject;

a visual acuity determination unit configured to, while determining the subjective refraction result, determine a first visual acuity of the at least one eye for a first applied refraction and a second visual acuity of the at least one eye for a second applied refraction, wherein the second applied refraction is different from the first applied refraction; and a sensitivity ascertaining unit configured to ascertain the sensitivity of the at least one eye taking into account the first and second visual acuities at the first and second refractions.

16. A non-transitory computer program product comprising computer-readable program parts which, when loaded and executed, cause a device for determining a sensitivity of at least one eye of a test subject to perform a method according to claim 1, wherein the computer program product at least partially controls and/or regulates a unit selected from a group consisting of: a refraction unit; a visual acuity determination unit; a sensitivity ascertaining unit; a controller; and an eyeglass lens data creation unit configured to create at least one individual eyeglass lens and/or to calculate at least one eyeglass lens surface from acquired measurement data.

* * * * *